United States Patent [19]

Koros et al.

[11] Patent Number: 5,167,223

[45] Date of Patent: Dec. 1, 1992

[54] HEART VALVE RETRACTOR AND STERNUM SPREADER SURGICAL INSTRUMENT

[76] Inventors: Tibor Koros; Gabriel Koros, both of 610 Flinn Ave., Moorpark, Calif. 93021

[21] Appl. No.: 405,371

[22] Filed: Sep. 8, 1989

[51] Int. Cl.⁵ .............................................. A61B 17/02
[52] U.S. Cl. .................................... 128/20; 74/422
[58] Field of Search ............... 128/17, 18, 20; 74/422; 269/227, 202; 254/95–97, DIG. 6

[56] References Cited

U.S. PATENT DOCUMENTS

| | | | |
|---|---|---|---|
| 2,053,868 | 9/1936 | Grosso | 128/20 |
| 2,670,732 | 3/1954 | Nelson | 128/20 |
| 3,030,948 | 4/1962 | Loeffler | 128/17 |
| 3,196,865 | 7/1965 | Rose | 128/20 |
| 3,221,743 | 12/1965 | Thompson et al. | 128/20 |
| 3,467,079 | 9/1969 | James | 128/20 |
| 3,486,505 | 12/1969 | Morrison | 606/90 |
| 3,572,326 | 3/1971 | Jensen | 128/20 |
| 3,656,364 | 4/1972 | Cable et al. | 74/422 |
| 3,731,673 | 5/1973 | Halloran | 128/20 |
| 3,810,462 | 5/1974 | Szpur | 128/20 |
| 3,916,907 | 11/1975 | Peterson | 128/345 |
| 4,050,464 | 9/1977 | Hall | 128/303 |
| 4,156,424 | 5/1979 | Burgim | 128/20 |
| 4,316,470 | 2/1982 | Braun et al. | 128/346 |
| 4,627,421 | 12/1986 | Symbas et al. | 128/20 |
| 4,726,356 | 2/1988 | Santilli et al. | 128/20 |
| 4,747,394 | 5/1988 | Watanabe | 128/20 |
| 4,852,552 | 8/1989 | Chaux | 128/20 |

Primary Examiner—Theatrice Brown
Assistant Examiner—M. Graham
Attorney, Agent, or Firm—Jessup, Beecher & Slehofer

[57] ABSTRACT

A generally U-shaped surgical instrument for prying apart and keeping open the rib cage in open heart surgery. There is a stationary arm with a toothed cross bar attached to it. A movable arm similar in configuration to the stationary arm has a housing at one end which slides on the bar and can be cranked open to force the sternum apart. The housing holds the crank mechanism and a pair of circular bearing inserts. The cranking mechanism is self-locking. One of the inserts is a safety feature, because it can be quickly popped out, should the movable arm become jammed on the bar during the cranking sequence, to provide clearance to unbind the arm on the bar. Both inserts are replaceable and take the wear and tear during the cranking process. New inserts can be inserted to refurbish the instrument. There is a V-clamp that slides on the arms and holds a support rod. There is a castellated clamp that slides on the support rod and it has an articulated extension rod. There is a self-centering universal clamp that slides on the extension rod and it holds a sternum spreader blade in position. All three clamps are used to adjust and hold a blade in position. There is also a boot clip that can be mounted on the arms for holding the web of sutures while the surgeon is sewing in an artificial heart valve.

5 Claims, 11 Drawing Sheets

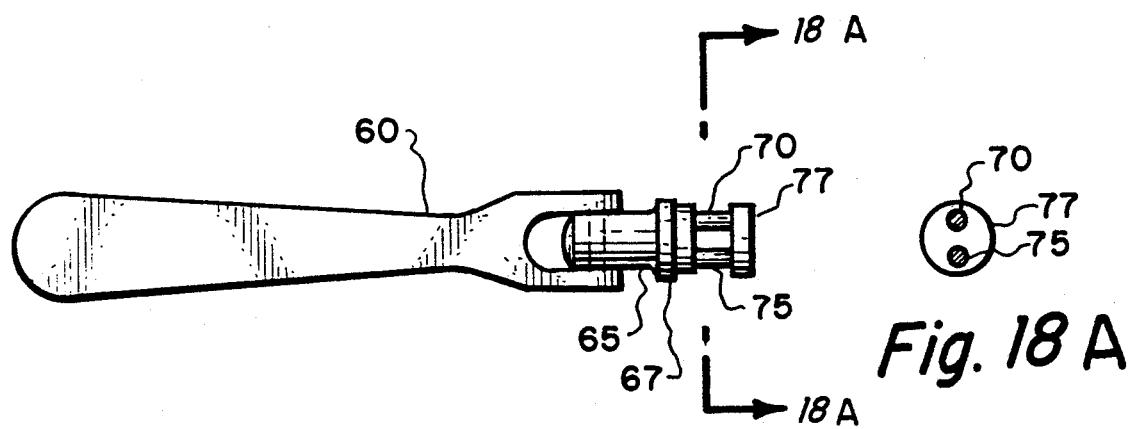
Fig. 18.
Fig. 18 A
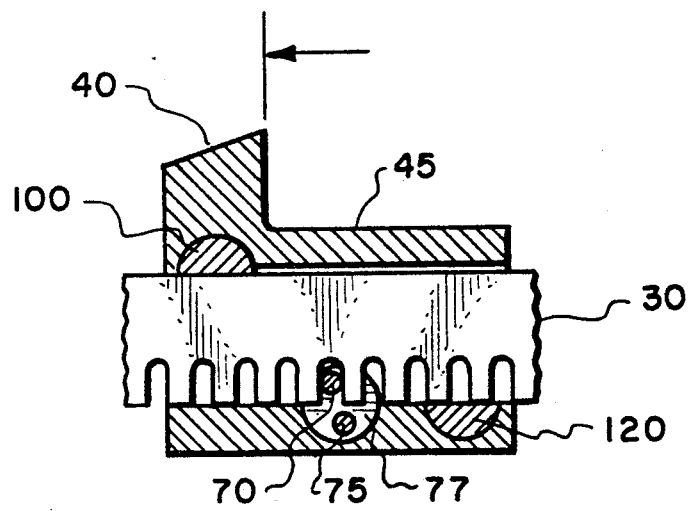
Fig. 19.

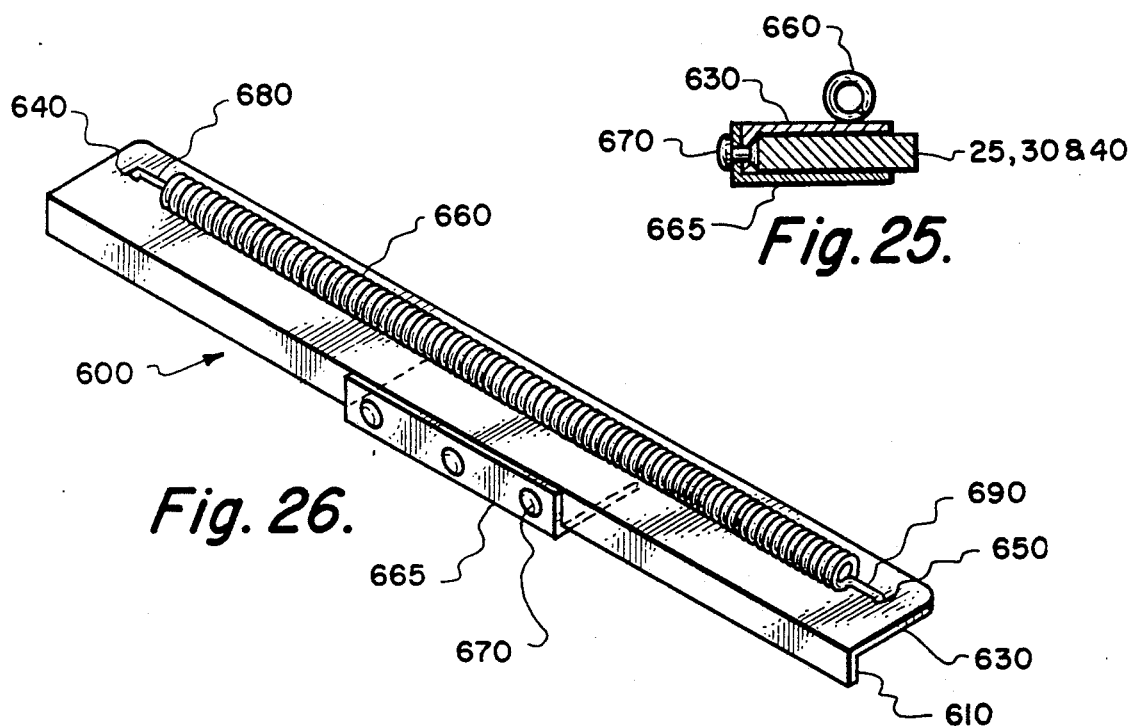

HEART VALVE RETRACTOR AND STERNUM SPREADER SURGICAL INSTRUMENT

BACKGROUND OF THE INVENTION

1. Field of the Invention

Surgery: surgical instruments; coaptators; hook-crack devices; serrefines; clamps; expanding arms.

2. Description of the Prior Art

The heart is the muscular organ that pumps the blood. The heart is divided into four chambers - two ventricles referred to as the left and right ventricle, and two auricles referred to as the left and right auricle. The blood flow through these four chambers is controlled by four valves. Two of the valves, the mitral valve and the aortic valve can become diseased through injury or infection, or either can be genetically imperfect. These two valves can be surgically removed and replaced with an artificial heart valve. Techniques nowadays include surgical machines or life support systems that are available in open heart surgery to allow the blood flow from the patient to be diverted to a heart-lung machine. The heart can be stopped while the surgeon performs surgery and repair upon the patient's heart.

The heart is contained within the thoracic, or chest cavity, and it is enclosed within a pericardium sac, which contains a fluid mixture that tends to lubricate the heart while it beats. The heart and pericardium are naturally positioned within the thoracic cavity underneath the body of the sternum, commonly referred to as the breast bone. The breast bone interconnects ribs 1 through 7 of the patient. In order for the surgeon to operate on the heart, he or she obviously has to have access to it. It is now standard procedure to access the heart by making a surgical incision beginning at the throat area and cutting medially the entire length of the sternum by incision and also by cutting through the sternum with a small electric saw. The gap created by the cut and separated sternum allows the surgeon to insert a sternum spreader (occasionally termed a retractor instrument) in between and the edges of the cut sternum. The sternum spreader (retractor) tool is cranked open until the two spreader arms, which abut the sternum edges, force the sternum and rib cage to separate and expand open giving access to the pericardium and enclosed heart within the thoracic cavity.

Artificial heart valves have a circular ring shape arc of the the following designs: a closed ball-and-cage; a tilting disk, and a pig valve in the ring.

SUMMARY AND OPERATION OF THE INVENTION

A generally U-shaped surgical instrument is used for prying apart and keeping open the rib cage in open heart surgery. There is a stationary arm with a toothed cross bar attached to it. A movable arm similar in configuration to the stationary arm has a housing at one end which slides on the bar and can be cranked open to force the sternum apart. The housing holds the crank mechanism and a pair of circular bearing inserts. The crank mechanism is self-locking. The crank mechanism, housing, and toothed cross bar are collectively termed the rack & gear means. One of the bearing inserts is a safety feature, because it can be quickly popped out, should the movable arm become jammed on the bar during the uncranking sequence, to provide clearance to unbind the arm on the bar. Both inserts are replaceable and take the wear and tear during the cranking process. New inserts can be inserted to refurbish the instrument.

There is a V-clamp that slides on either arm, and the clamp holds a support rod. There is a castellated clamp that slides on the support rod, and it has an articulated extension rod. There is a self-centering universal clamp that slides on the extension rod, and it holds a retractor blade in position. All three clamps are used to adjust and hold a heart valve retractor/blade in position. There is also a boot clip that can be mounted on the arms and cross-bar for holding the web of sutures while the surgeon is sewing in an artificial heart valve.

Expressed another way, the present invention comprises a heart valve retractor and/or sternum spreader used as a surgical instrument by the surgeon in an operating room to facilitate the surgeon in opening up the chest cavity of the patient and operating on the patient's heart to replace the aortic valve or the mitral valve with an artificial heart valve. The sternum spreader can be used without the valve retractors in by-pass surgery, open heart surgery, or heart transplant surgery.

The candidate for open heart surgery is initially prepped for the operating room. After being anesthetized, wired up to various monitoring instruments, and various intravenous needles inserted, the patient is placed in a prone position face up on the horizontally raised operating table. The team of surgeons begin their work by initially making a medial incision down the center of the chest with a cauterized scalpel beginning at the base of the throat and cutting down past the medial portion of the sternum or breastbone. After the surgeon has cut down to the breastbone, he switches to a small hand-held electric saw to cut the sternum. After this incision and cutting away has been completed, the surgical team can begin to open up the sternum to get to the thoracic cavity of the patient. The present invention, the sternum spreader, is intended to be placed into the surgically slit opening or gap in the sternum and to mechanically and physically spread and pry apart the rib cage to provide access to the heart and pericardium area. A cavity is opened up about 6 to 8 inches across. The sternum spreader spreads apart by turning a crank on the instrument.

The present invention comprises a toothed cross bar having one end connected at a right angle to one end of a rail shaped bar or arm. The two pieces are integrally joined and are referred to as an L-shaped arm comprising the stationary portion of the spreader. The toothed bar has attached to it an arm in parallel relationship with the stationary arm and is moveable in a parallel relation to the stationary bar by means of slideably engaging the toothed cross bar. The base of the slideable arm forms a housing having a slotted opening for allowing the toothed bar to pass through. The housing also holds several components including the pivot shaft and pins for the swing handle collectively referred to as the crank; a pair of load bearing swivel inserts; and a portion of the toothed cross bar. Extending from beneath both the stationary arm and the movable arm are four (4) sternum blades which are shaped in such a way to have their openings press against the cross sections of the sawed halves of the sternum and to function as the spreader's contact points with the cut edges of the sternum as the stationary arm and the moveable arm are slowly spread apart by the cranking action of the spreader.

The spreading action is accomplished by turning the swing handle that is attached to the pivot shaft collectively called the crank which in turn causes the housing of the moveable arm and the moveable arm to traverse along the toothed cross bar. As the stationary arm and the moveable arm spread apart, both will spread apart evenly so that they are equally positioned on either side of the spreading rib cage. After a sufficient number of turns of the swing handle have taken place, the swing handle will automatically retain the moveable arm at that position on the toothed cross bar where the surgeon wants to be keep it. The crank is self-locking.

Attached to both of the arms are a pair of rail clamps known as V-clamps. These V-clamps hold a support rod in a parallel relationship with either arm to which the V-clamp is clamped to. The support rod further has secured to it a right-angled castellated clamp. The right-angled castellated clamp interconnects the support rod with an articulated extension rod which extends above the heart when the spreader is in position. The castellated clamp, when loose, can slide back and forth on the support rod and can also angularly adjust and set the extension rod. The extension rod further has attached to it a third clamp which is referred to as a self-centering universal clamp. The self-centering universal clamp further holds one of two blades referred to as an aortic valve retractor blade or a mitral valve retractor. By means of the V-clamp, the right angle castellated clamp, the self centering universal clamp, and the extension arm and parallel support rod, the surgeon can, after making the appropriate incision in the heart, manipulate and set at a stationary position and clamp down the mitral valve retractor and/or the aortic valve retractor blade so that the heart muscle is pulled away and mechanically held open by means of the invention so that the surgeon can proceed to replace a diseased heart valve with a new artificial one.

Another feature of the invention is a valve suture boot clip which clips on to either one of the moveable or stationary arms, or the toothed cross bar. The surgeon can place a sterilized net underneath the heart and have the circumference of the net large enough to contact the sternum spreader. Individual filaments of the net can be secured to the boot clips, because each boot clip comprises a coiled spring which can be spread apart at individual coils to temporarily anchor a piece of filament of the net. The net can be removed in an easy fashion by pulling it away from the boot clips. The net is pulled up around its circumference and clipped on to the boot clips. This also lifts the heart up in the thoracic cavity and suspends it to provide better access to the heart for the surgeon.

The boot clip also has utility when the surgeon is suturing an artificial heart valve into place. A typical artificial heart valve is ring-shaped, and it has approximately 100 to 200 color coded separate suture threads which have already been tied around the ring-shaped portion of the artificial heart valve. The sutures for a web when radially placed on a flat surface. In order to maximize the safety of the inserted artificial heart valve, each suture should be individually tied off, should one break and become disengaged. The purpose of the radially positioned suture threads is to allow the surgeon tie off each thread one at a time. Unfortunately, when there are 100 suture threads extending from the artificial heart valve, it becomes quite a jumble of threads to have the surgeon keep track of the color matched threads.

The boot clip is an elongated section of metal shaped like a channel bar. It has an elongate rectangular flat top, a back edge, and a resilient clip which can bend apart sufficiently to clip over the edge of the arm or the toothed cross bar, and hold the boot clip in place. The top has a coil spring mounted lengthwise. The hooked ends of the coil spring are secured to two holes in the top. The distance between both holes is slightly greater than the overall length of the spring causing the spring to be slightly tensioned when installed. Each adjoining coil in the spring is sufficiently flexible to spread apart to grip and anchor a filament or thread temporarily, and yet allow the filament to be removed without damaging the thread.

Another purpose of the valve suture boot clips is to allow the surgeon to position the individual suture threads of the artificial heart in a radial fashion and have the ends of them temporarily clipped or secured to the spring portion of the boot clip. This allows the surgeon to individually remove the threads one at time from the boot clip, suture it, tie it off, and clip it off, and then proceed in a circular fashion to suture all of the suture threads.

After the artificial heart valve(s) has been surgically implanted, then the remainder of the operation is to retract and remove the valve retractor/sternum spreader and to close up the patient. Unfortunately, the valve retractor/sternum spreader can bind or become jammed in its open position while attached to the patient. If the patient is a large individual and when the stationary arm and the moveable arm are spread apart by cranking the swing handle on the moveable arm, occasionally the toothed bar can become sufficiently bowed or bent to the point where the surgeon cannot retract the moveable arm to its closed position, because the housing of the moveable arm becomes jammed and otherwise cannot traverse the toothed cross bar. The stationary arm and moveable arm put force on the toothed bar because the sternum and rib cage resist being spread apart.

As part of the present invention, there are inserted in openings within the housing portion of the moveable arm adjacent to the toothed cross bar and the pin shaft of the swing handle, a pair of load bearing swivel inserts, one on either side of the toothed cross bar. They are staggered so that they are not parallel with each other. If the moveable arm becomes jammed on the toothed cross bar, then the surgeon can remove one of the swivel inserts by means of unscrewing a phillips screw which dismantles the insert, and it can be popped out to provide some clearance between the toothed cross bar and the slotted opening in the housing, thereby allowing the crank to be turned to retract and close the moveable arm against the stationary arm. The load bearing swivel insert on the other side of the rack can swivel or turn within its opening to allow the housing to tilt relative to the toothed bar.

The load bearing inserts have other applications because a typical valve retractor/sternum spreader has a useful life of up to ten years in the operating rooms. After repeatedly opening and closing the the moveable arm by turning the cranking mechanism, wear takes place in the hollow rectangular opening in the housing of the moveable arm and on the toothed bar itself. After too much wear and tear has taken place, then the connection becomes too loose to be of any further use. By means of these replaceable load bearing swivel inserts, the instrument can be refurbished by replacing the two load bearing surfaces as they eventually wear away to keep the tolerance between the moveable arm housing and the toothed bar to the minimum as required to by the original specifications for the surgical instrument.

The self centering universal clamp is also an important feature to this invention, because the components are such that they will always reassemble to their original position. After the heart valve retractor/sternum spreader surgical instrument and accessories are used in an operation, they have to be disassembled, autoclaved, sterilized, and reassembled for use in the next operation. The parts comprising the instrument have to be reassembled in the proper sequence and order as the instrument was intended to be used.

BRIEF DESCRIPTION OF THE DRAWINGS

FIG. 18 discloses a side view of the swing handle and the pivot shaft. Section A—A of FIG. 18 is also illustrated.

FIG. 19 shows a partial sectional view showing the relationship between the housing of the moveable arm with the toothed bar in place and the handle pins of the pivot handle and how they interact and cooperate with the teeth and tooth spaces of the cross bar.

FIG. 25 illustrates a cross-sectional view of the boot clip taken along the lines 25—25 of FIG. 1 showing the clip secured to one of the arms. The boot clip holds the web of sutures, or the netting for uplifting the heat during the operation.

FIG. 26 illustrates a perspective view of the boot clip.

DETAILED DESCRIPTION OF THE INVENTION

Figure 1:
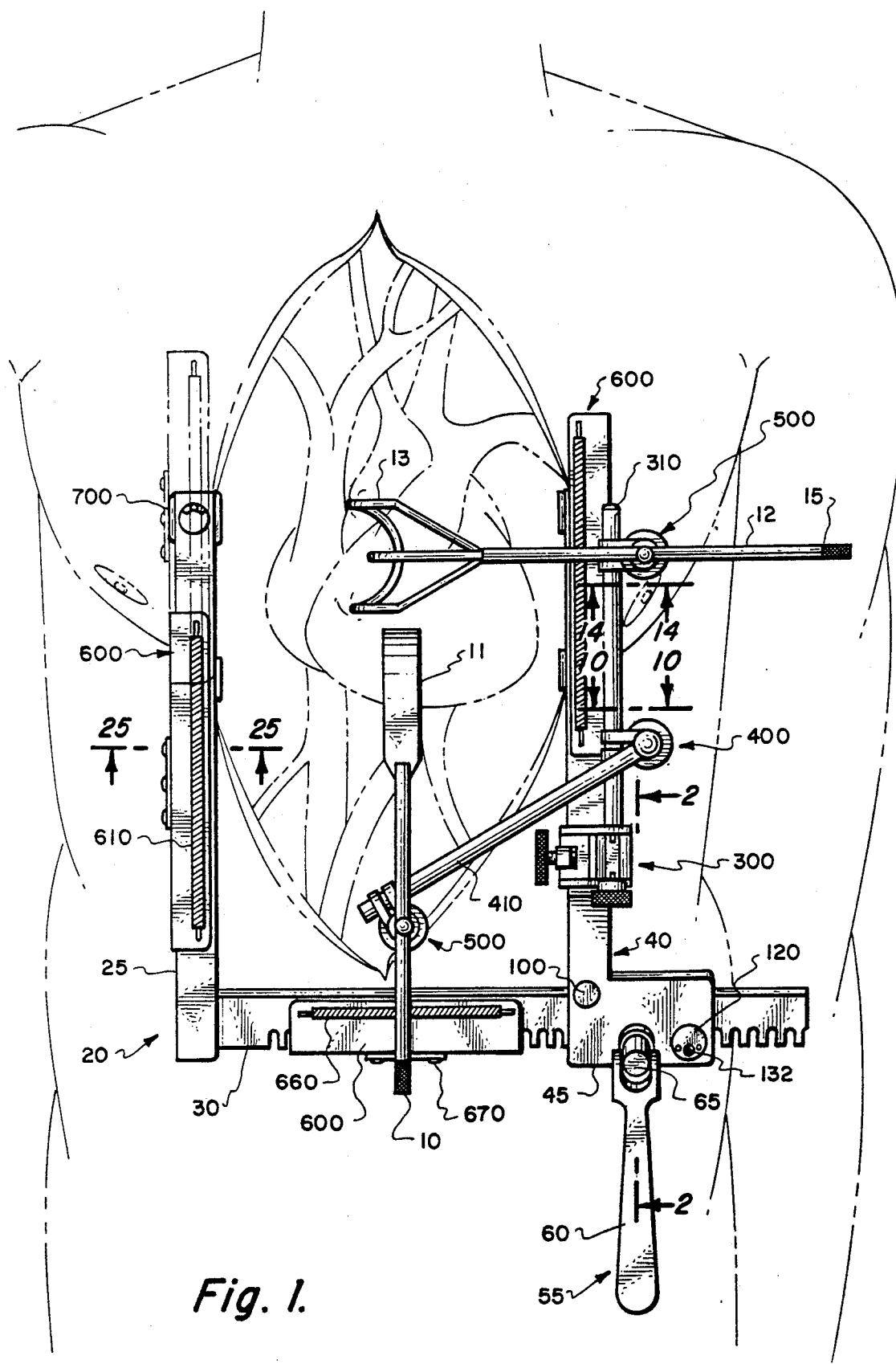
FIG. 1 is a top plan view of a patient undergoing open heart surgery and about to undergo heart valve replacement. The valve retractor/sternum spreader is correctly positioned in place with the mitral valve retractor and the aortic valve retractor positioned over the heart of the patient.

Referring now to FIG. 1 there is illustrated the present invention WHEN it is used as a surgical instrument in open heart surgery to replace a damaged heart valve with an artificial one. sternum spreader can also be used in by-pass surgery, aneurysm heart wall repair or heart transplant surgery.

With minor modifications, the present invention can also be used in: lumbar laminectomy surgery; neck surgery; stomach surgery; rib surgery; and sternum surgery.

When the present invention is used in open heart surgery, the front medial chest area of the patient, referred to as the sternum, or breastplate, initially is cut medially along the sternum and further is cut away to sever the sternum to allow access by the surgeon into the thoracic or chest cavity area and the pericardium portion where the heart is positioned within the body. In FIG. 1, the rib cage is spread, or pried apart, and kept open by means of the present invention. Illustrated in the thoracic cavity is the patient's heart and supportive blood vessels show in dashed or phantom lines.

Figure 23:
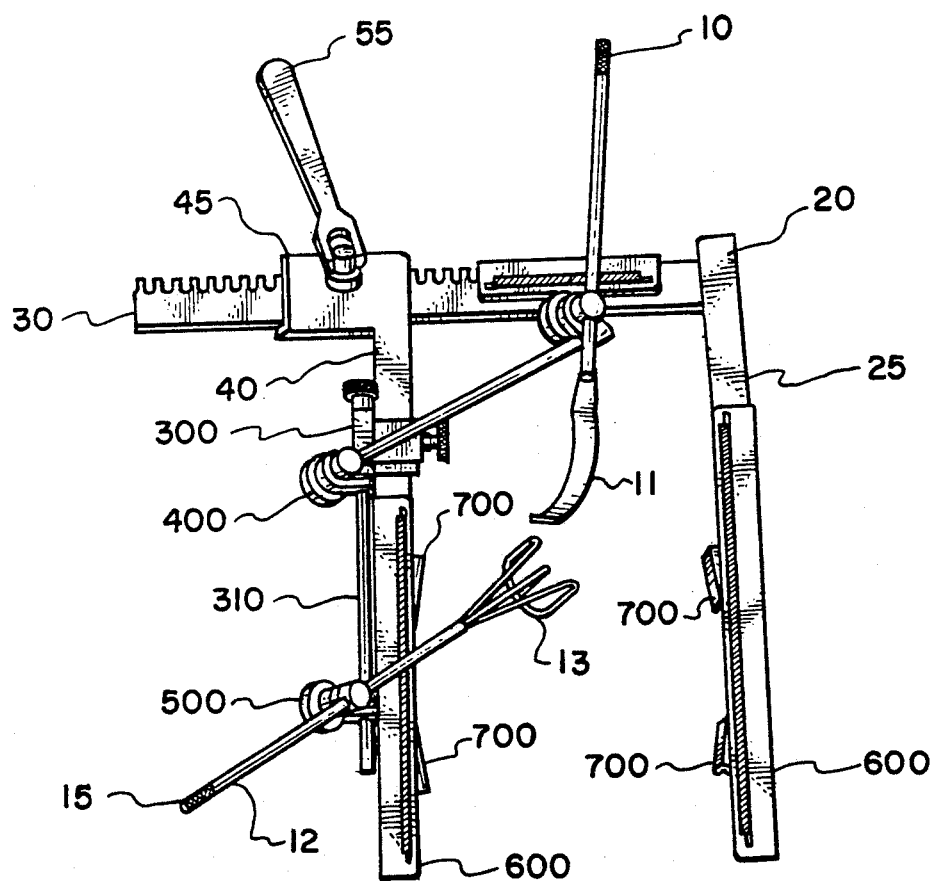
FIG. 23 illustrates the embodiment of the present invention the aortic valve retractor and the mitral valve retractor as they would probably be used by a surgeon in open surgery, and clearly illustrating the boot clips.

The present invention is entitled a Valve Retractor/-Sternum Spreader. The surgical instrument is shown and it generally has a U-shaped appearance. It is optional for the surgeon to place the toothed cross-brace transversely over the abdominal area (see FIG. 1) or transversely along the upper chest area (see FIG. 23) of the patient. The instrument is used to spread apart the sternum area where the incision has been made and to mechanically keep the sternum spread apart to allow access into the thoracic cavity by the surgeon. Additionally, there are two retractors shown in FIG. 1. One is entitled the aortic valve retractor 10, which has a serrated hook at one end of a shank 12. The other one is referred to as the mitral valve retractor 15, which has a semi-circular basket 11 at one end of a shank 11. In order for the surgeon to replace a diseased valve with an artificial one, it is necessary to incise the wall of the heart muscle and to physically spread apart the portion of the heart wall along the incision so that the surgeon can physically enter the chamber or chambers of the heart. This is termed the intracardiac portion of the operation. The purpose of the mitral valve retractor 15 and the aortic valve retractor 10 is to physically hold open portions of the heart along the incision and to hold the subject heart valve in position to allow the surgeon access while he is working on removing the diseased valve and replacing it with an artificial heart valve.

In the past, it was necessary for surgical assistants to physically hold open the sternum and portions of the heart wall by manually holding onto the various sternum spreader blades used in the past. By means of the present surgical instrument, along with the retractors after the sternum has been spread apart, the retractors can be manually positioned and tightened down by means of the clamps, and to reposition them as necessary during the course of the operation.

The present invention comprises an L-shaped stationary section 20 which has a stationary vertical arm 25 and a horizontal toothed cross bar 30. A moveable arm 40 traverses along the toothed cross bar 30, and the moveable arm 40 can move towards or away from the stationary arm 25. The moveable arm 40, and the stationary arm 25 are both in a parallel relation to one another. The moveable arm has a housing section 45 at its lower end and has a rectangular hollow passage 50 for allowing the toothed bar to pass back and forth through it. There is a rack and gear means 55 illustrated as a swing handle 60 and crank mechanism demountably secured in the housing which will cause the moveable arm 40 to traverse back and forth along the toothed cross bar 30 by means of cranking the swing handle 60. The swing handle is connected to a pivot shaft 65 by a pivot pin 61. The swing handle 60 has attached to it, and inserted into the housing section of the moveable arm, a pivot shaft 65 having two pins 70 and 75 at the shaft's end for meshing with the teeth 80 on the toothed cross bar 30. Within the housing are two load bearing swivel inserts 100 and 120 that maintain the housing and therefore the moveable arm in a right angle attitude relative to the toothed bar. The load bearing inserts 100 and 120 are intended to be removable to allow the bar to move on the toothed cross bar 30 in the event of jamming or binding of the moveable arm on the toothed bar.

Figure 8:
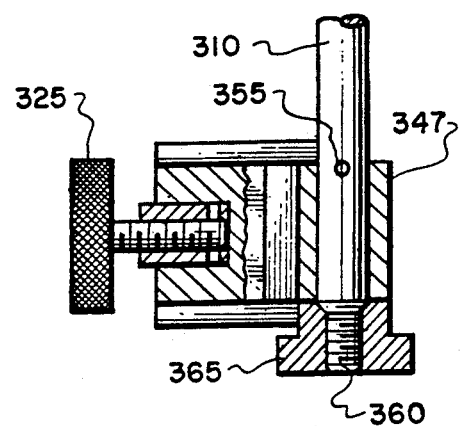
FIG. 8 is a fragmentary cross-sectional view taken along the lines 8—8 of FIG. 7 further disclosing the components of the V-clamp, or side arm clamp.
Figure 9:
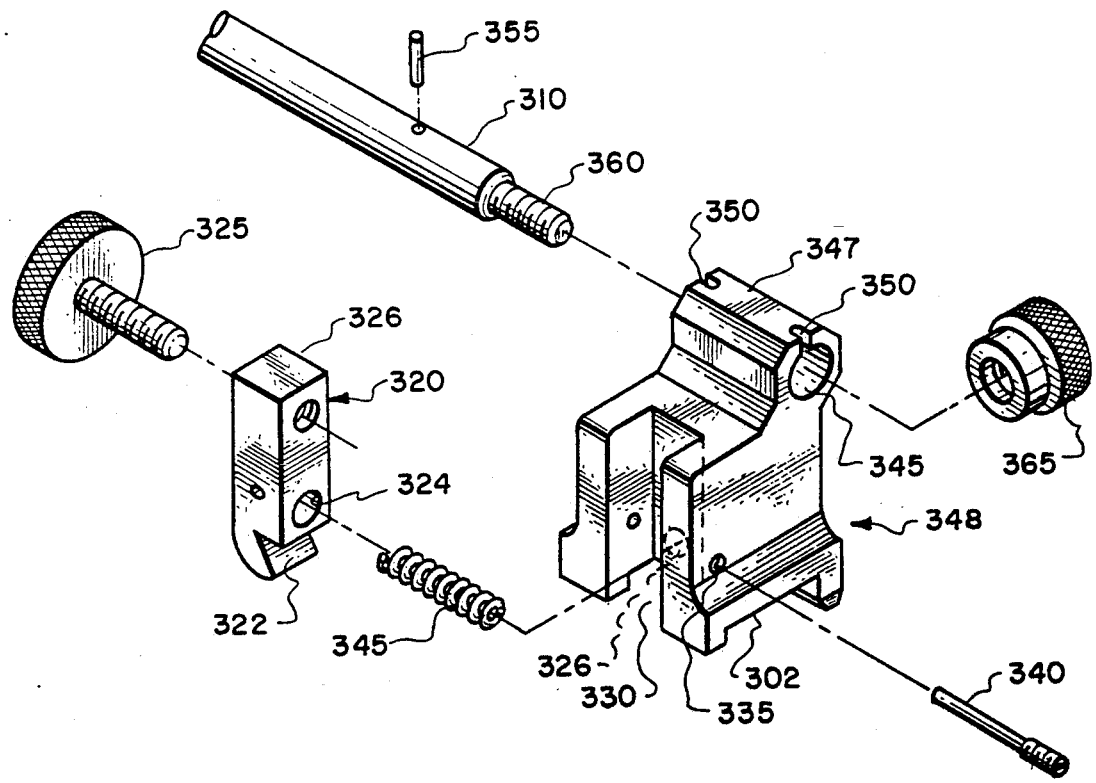
FIG. 9 is a exploded perspective view showing the interrelationship between the V-clamp, the side arm support rod, and the components comprising all the elements of the V-clamp.
Figure 10:
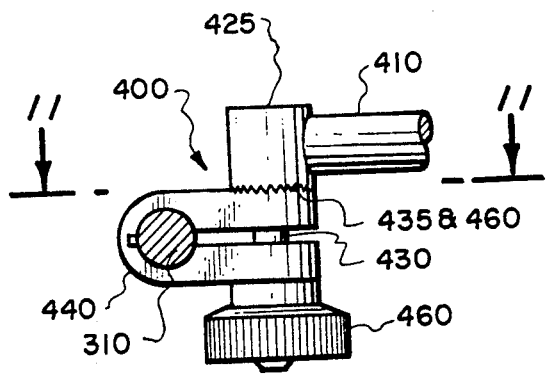
FIG. 10 is a elevational view taken along the lines 10—10 of FIG. 1 showing the castellated extension arm clamp.
Figure 11:
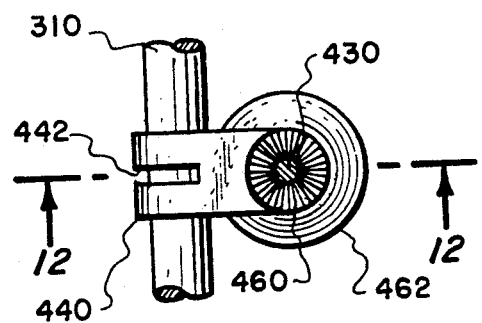
FIG. 11 is a view taken along the lines 11—11 of FIG. 10 showing the top plan view of the castellated clamp.
Figure 12:
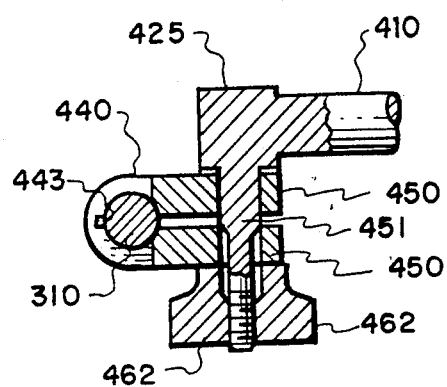
FIG. 12 is a view taken along the lines 12—12 of FIG. 11 showing the cross-sectional view of the castellated clamp.
Figure 13:
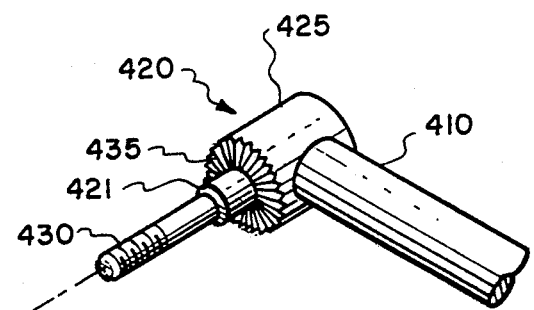
FIG. 13 is an exploded perspective view showing the three major components of the castellated clamp.
Figure 13:
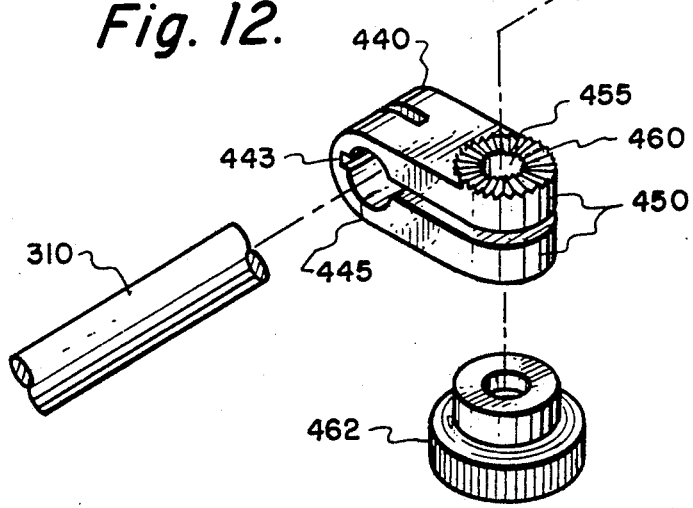

There are also three clamps as part of the present invention and are illustrated in FIG. 1. The first clamp is referred to as a side arm clamp 300, or V-clamp, which is illustrated in detail in FIGS. 7-9. The second clamp is referred to as a right-angled castellated clamp 400 which is shown in detail in FIGS. 10-13. The third clamp is referred to as a self-centering universal clamp 500 and is shown in detail in FIGS. 14-17. The V-clamp can be clamped onto either of the arms 25 & 40, and it can slide back and forth on either one of the arms because of its V-shaped channel configuration in the clamping portion. It functions to hold a support rod 310 above either arm and parallel to either arm. The support rod 310 in turn has the castellated clamp 400 secured to the rod. The castellated clamp 400 in turn has an extension rod 410 extending from it. The castellated clamp can slide back and forth on the support rod 310 and it can also allow the extension rod 410 to be moved in an angular, articulated fashion relative to the support rod 310 and arms 25 & 40. The third clamp 500 interconnects the extension rod 410 on the castellated clamp 400, with one of the retractors 10 or 15. The third clamp, which is referred to as a self-centering universal clamp 500, allows the surgeon to angularly change the position of either the mitral valve retractor 10 or the aortic valve retractor 15, and also to extend or retract either one of them relative to where the universal clamp 500 is spatially oriented. By means of these three clamps, which are all secured to the arms 25 & 40 directly or indirectly, the surgeon can independently manipulate either one of the retractors 10 or 15 and lock it into position in any orientation he desires. The final component of this invention is referred to as a boot clip 600. The boot clip snaps onto either one of the arms 25 & 40, or onto the toothed bar 30. It has a clip-on feature so that it can be readily clipped on and clipped off at the option of the surgeon and is moveable along the component it is secured to. On the upper surface of the boot clip is a slightly stretched coiled spring 660 secured at both ends to the boot clip 600. The individual coils of the spring can be spread apart to temporarily hold and anchor a piece of thread or piece of netting to the boot clip 600. FIG. 1 shows the boot clip on the stationary arm 25 in two positions. The second position is sketched in phantom lines to indicate that the clip is slideable along the arm.

Figure 22:
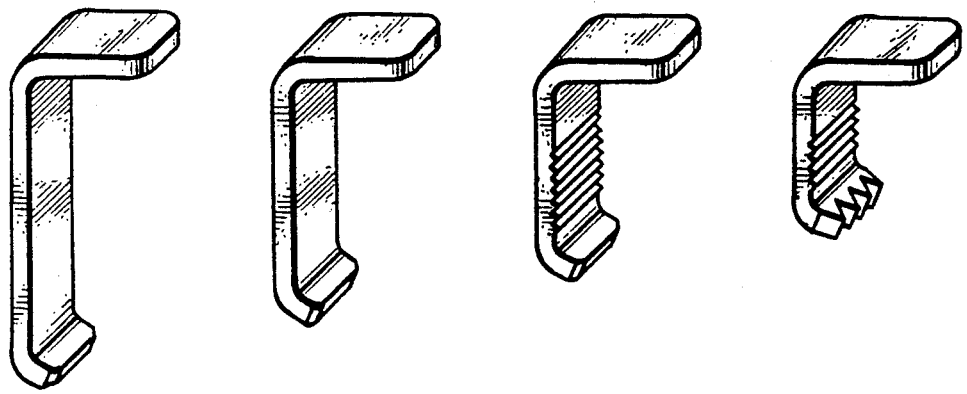
FIG. 22 shows various embodiments of the swivel blades that extend beneath both arms of the sternum spreader and abut against the edges of the cut sternum and force and push the sternum as the sternum and rib cage are being spread responsive to the two arms expanding apart.
Figure 24:
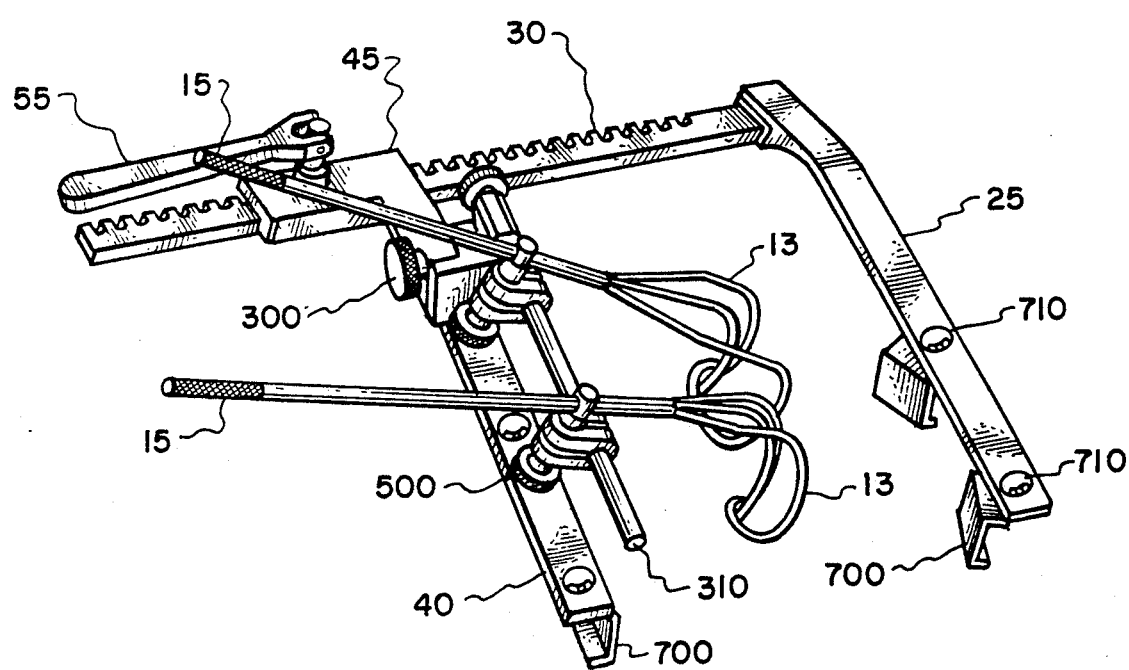
FIG. 24 illustrates the HEART VALVE RETRACTOR & STERNUM SPREADER SURGICAL INSTRUMENT illustrated in FIG. 1 from another perspective without the mitral valve retractor or the castellated clamp shown.

Extending from below the stationary arm 25 and the adjustment arm 40 are two rows of sternum blades 700 extending from below either arm and which are swivelly mounted to both of the arms. The blades 700 come in various sizes, but they generally have a channel-shaped cross section. Various sizes and shapes are illustrated in FIG. 22 without any swivel connections shown. These sternum blades 700 can pivotally adjust and conform independently to the sternal edges created by the surgeon in the initial incision and cutting of the sternum bone. The faces of blades hold the sternum edges in place and keep the sternum spreader in position as the sternum and rib cage are being spread apart to open up the chest cavity for the surgeon. The sternum blades are shown in FIG. 22 without their swivel connections 710. They are shown with their swivel connections in FIG. 24.

Figure 2:
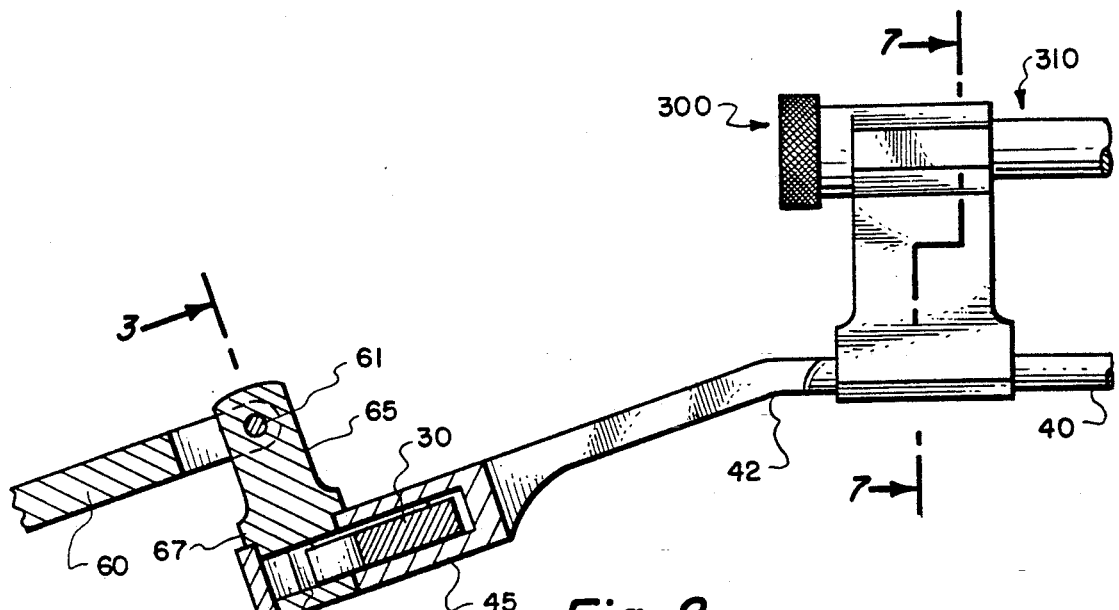
FIG. 2 is a sectional view taken along the lines 2—2 of FIG. 1 showing the cranking mechanism and the toothed cross bar in the housing of the moveable arm cut away.
Figure 4:
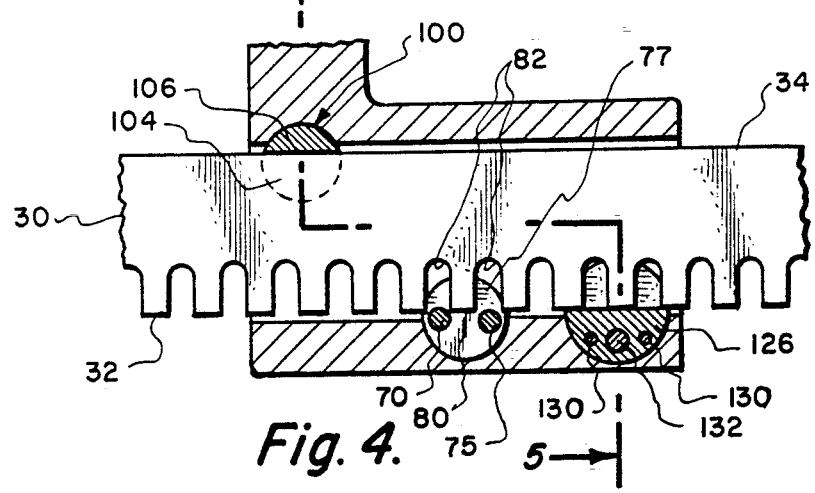
FIG. 4 is a top plan fragmentary view taken along the lines 4—4 of FIG. 3 showing the two load bearing swivel inserts and a portion of the pins of the swing handle cooperating with the toothed bar component of the invention.
Figure 3:
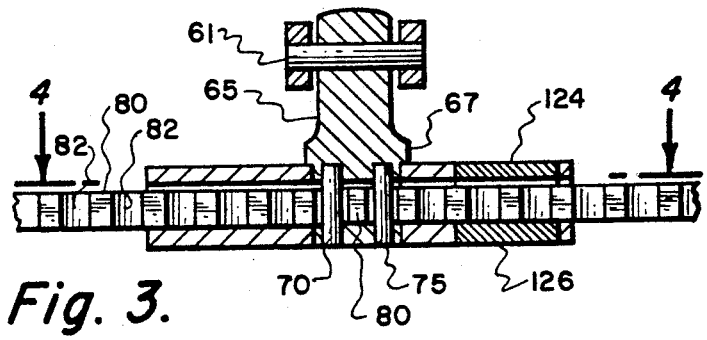
FIG. 3 is a sectional view taken along the lines 3—3 of FIG. 2 showing the base of the swing handle with the handle pins mating with the toothed cross bar.

The moveable arm 40 and the stationary arm 25 are both curved or angled to fit the body contour. The sternum and chest area both have a curved shape in their longitudinal profile. The curved area or angled portion 42 of the moveable arm can be clearly seen in FIGS. 2 and 24 and which show the housing of the moveable arm at an angular attitude relative to the remaining portion of the moveable arm. The view in FIG. 2 shows the partial cross-sectional view exposing the rectangular slotted opening 50 through which the toothed cross bar 30 passes back and forth in the housing 45 of the moveable arm 40. This is also seen in the perspective exploded view of FIG. 6 and the cross-sectional view in FIG. 5. The overall dimensions in cross section of the toothed cross bar 30 are slightly smaller than the cross-sectional dimensions of the slotted opening 50 in the housing. The housing 45 can slide back and forth on the toothed bar. There is only a slight amount of tolerance between the toothed bar and the slotted opening. There cannot be too much tolerance in this moveable joint, because this area takes a lot of the torque and force which is exerted because the moveable arm has sternum blades 700 pressing against the cut sternum and rib cage as it is being pried open. The pressure against the sternum blades 700 caused by the rib cage's resistance to being open creates an opposing force on the moveable arm 40. The force in turn is transferred to the housing and toothed bar section. There is also force exerted against the sternum blades 700 of the stationary arm 25. The forces exerted against both arms by the expanded rib cage creates stress on the interconnecting cross bar 30. When a surgeon is operating on a person who is large and obese, or has a strong sternum and rib cage area, the cranking action of the swing handle 60 while prying open the rib cage creates quite a bit of force and stress on the toothed cross bar 30. Occasionally the stress is so great that the toothed bar actually becomes permanently bent, slightly bowed, or warped as the surgeon is cranking open and spreading apart the sternum and rib cage. At that juncture the surgeon has no way of knowing that a problem has developed in the sternum spreader He proceeds with the operation until it is complete and then when the patient is ready to be closed up, the surgeon realizes to his horror that, as he is attempting to uncrank the swing handle, the moveable arm and its housing is binding on the toothed bar thereby preventing the housing 45 and attached moveable arm 40 from retracting back to its at-rest closed position and thereby preventing the patient from being closed up so that the operation can be completed. Under these circumstances, in the prior art devices, the operating team had no alternative but to physically saw off the moveable arm adjacent to the housing so that the moveable arm could be collapsed back to its at rest position. This, of course, is a dangerous predicament because of the introduction of possible infection and unwanted material into the patient's chest cavity. At the very minimum, it results in unnecessary delay in the operation, thereby endangering the life and safety of the patient The emergency situation of having a binding moveable arm that is jammed or binding and cannot retract along the cross bar can be avoided by including a pair of load bearing swivel inserts 100 and 120 as shown in FIG. 6. In the present invention, there is a certain amount of slack or tolerance between the toothed edge 32 and the back edge 34 of the toothed arm bar 30 and the walls of the slotted opening 50 in the housing of the moveable arm. In the housing there are also three cylindrical holes 102, 103, and 122 drilled through the top and bottom of the housing. The purpose of the two staggered off-setting drill holes 102 and 122 in the housing is for the insertion of what are termed load-bearing wear and swivel inserts 100 and 120. The first bearing insert 100 is cylindrically shaped and has a secant flat 104 or gap cut away laterally for creating a sliding surface. The secant flat 104 has a width slightly larger than the thickness of the toothed bar 30 so that the toothed bar can freely slide back and forth in the secant flat cut away 104 in the first bearing insert 100. Additionally, the flat face 106 at the base of the secant flat can have a hard metal welded to it to create the hard surface interfacing with the back edge 34 of the toothed bar and the bearing surface to provide in a long wearing relationship between the two. The cross bar 30 is manufactured from stainless steel.

The other load bearing insert 120 is positioned in the third cylindrical hold 122 in the housing and is a larger diameter load insert than insert 100. and has a secant flat. However, the second load bearing insert 120 has a circular cap 124 which is removable from the body 126 of the load bearing insert 120. The circular top is fastened to the body of the load bearing surface by small pin holes 128 with two alignment pins 130 positioned in them to keep the circular cap 124 in a stationary relationship with the lower body 126 of the load bearing insert. There is also a phillips screw 132 that manually keeps the circular cap 124 secured to the lower body 126 of the second load bearing insert 120. Insert 120 also has a flat face formed as part of a ledge on the body 126.

Figure 5:
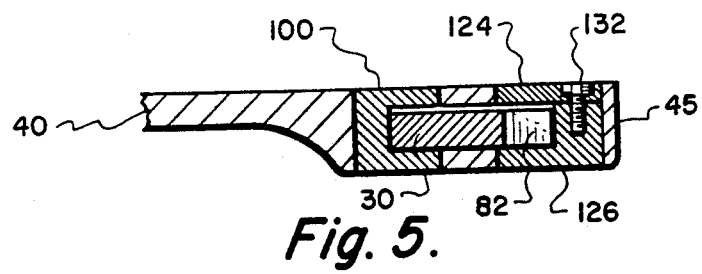
FIG. 5 is a fragmentary sectional view taken along the lines 5—5 of FIG. 4 further illustrating the load bearing swivel inserts in the housing of the moveable arm of the device.
Figure 6:
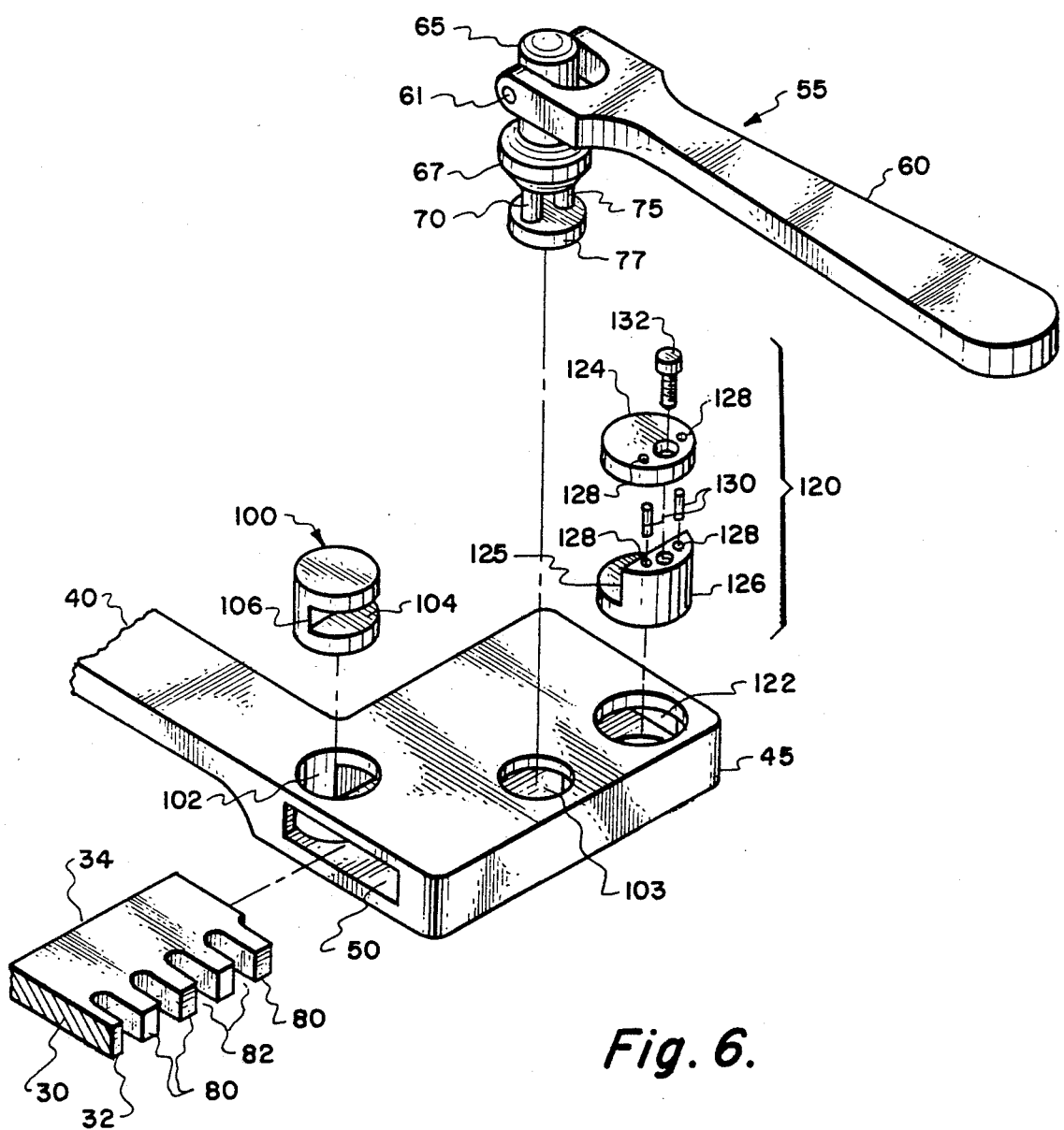
FIG. 6 is an exploded perspective view showing a portion of the arm, the toothed bar, the swing handle and pin combination, and the two swivel inserts.

The relationship between the two load bearing wear inserts 100 & 120, and the toothed bar 30 is shown in FIG. 5. The staggered inserts effectively function as a guideway or track within the rectangular slotted opening 50 in the housing 45 of the moveable arm 40. The main purpose of this arrangement of having the circular inserts is in the emergency situation where the moveable arm binds or otherwise becomes jammed during the operation and the two arms 25 and 40 will not close with one another. In that emergency situation, the surgical team simply has to remove the screw 132 securing the circular cap 134 to the second load bearing insert, remove the cap, and push out the lower body 126 with the flat face 125 of the load bearing swivel insert. After the second load bearing insert is removed, then there is sufficient room or clearance within the housing so that the housing can pivot or rock back and forth on the toothed bar to allow the surgeon to uncrank the moveable arm and housing along the toothed bar to retract and collapse the sternum spreader instrument.

Figure 20:
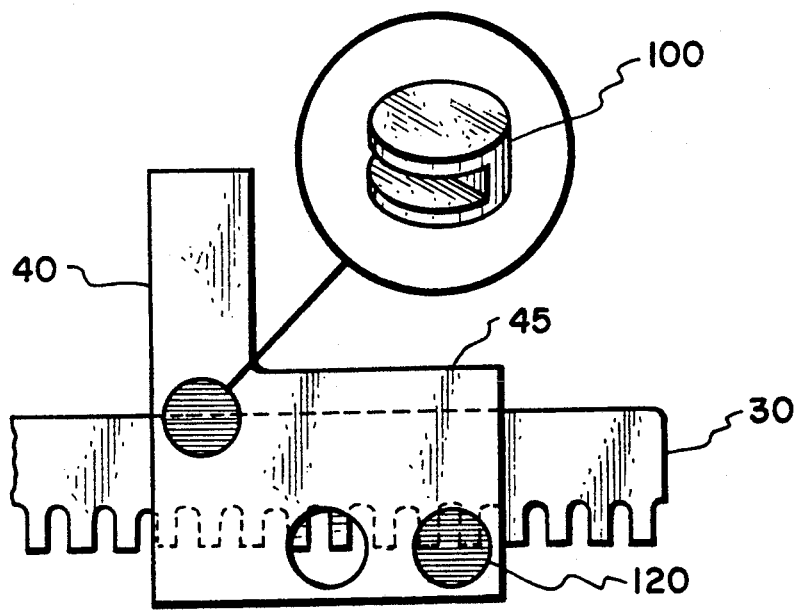
FIG. 20 shows where the swivel inserts are inserted in the of the moveable arm and how they cooperate with and align section of the toothed bar in the housing.
Figure 21:
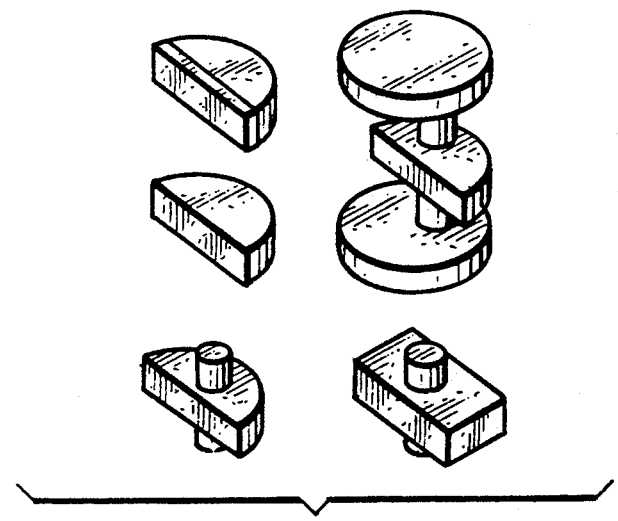
FIG. 21 shows various embodiments of the different types of swivel inserts which could be adapted and positioned in the housing of the moveable arm.

Yet another purpose for the load bearing inserts is to provide a longer useful life for the sternum spreader instrument. In the course of normal usage of a sternum spreader over a period of years, the frictional grinding and the stresses placed in the slotted opening inside the housing and on the toothed bar causes some wearing away at the contact surfaces. By means of having two load bearing inserts 100 and 122 positioned in the housing, these are the only two contact areas between the toothed bar and the housing of the moveable arm when the sternum spreader is in use. This relationship is illustrated in FIG. 20. These removable load bearing inserts can be removed and replaced with new bearing inserts, which will have the same specifications and tolerances as the originals. The toothed bar is manufactured from a sufficiently hard metal such as stainless steel so that it will not wear relive to the load baring surfaces. Either load bearing wear insert is available in a variety of shapes, sizes and metallurgical composition. FIG. 21 illustrates representative inserts such as: semi-circular; rectangular; or single decked, double-decked, or triple-decked with a pivot pin. The sliding surfaces 106 or 125 of the inserts can be overlaid with a tungsten carbide surface for a long lasting insert. The bearing can be cast from 55 series bronze, which is a self-lubricating alloy. This type of alloy is softer and wears out quicker than tungsten carbide, however.

Another feature disclosed in the present invention is the cranking mechanism which functions to move the housing along the toothed bar. The cranking mechanism is illustrated in FIG. 18. The cranking mechanism 55 has a swing handle 60 that it is pivotally attached to the pivot shaft 65 at a generally right angled position. The pivot shaft extends into the middle circular opening 103 in the hosing. The circular opening is drilled through both faces of the housing. There is a circular flange 67 at the upper end of the pivot shaft 65 which rests against the upper face of the housing so that the pivot shaft is limited by how far it can enter into the housing. The two pivot pins 70 and 75 extend longitudinally from the flanged retaining portion 65 and at the bottom there is a circular retaining plate 77. The circular retaining plate prevents the shaft from disengaging from the toothed bar 30 and being pulled out of the housing 45 while the toothed bar 30 is in the slotted opening 50 of the housing. The dimensions are such that the two pins exactly fit adjacent spaces, or lands 82, between a given tooth 80 on the toothed bar 30. When the pivot shaft 65 is rotated by means of having the surgeon rotate the swing handle 60, the movement of the two pivot pins is such that they will work their way into adjacent spaces 82 of a tooth 80 and sequentially cause the housing 45 to move along the toothed bar in response to the rotation of the crank and thereby the pivot shaft. This is illustrated in FIG. 19. The retaining pins 70 & 75 also preclude the separated spreader arms 25 & 40 from collapsing back together even when no one is holding the handle to prevent it from turning, that is, when there is no torque applied to the handle. The crank handle mechanism does not require a separate lock down means to prevent the swing handle mechanism 55 from automatically uncranking in response to the open sternum trying to close itself manually and thereby closing the open arms. This cranking mechanism is self-locking in the sense that the pivot shaft and the two pins 70 & 75 will not rotate or move relative to the toothed bar 30 unless someone manually rotates the pivot shaft by means of the crank handle either clockwise or counterclockwise.

DETAILED DISCUSSION OF THE CLAMPS

Figure 7:
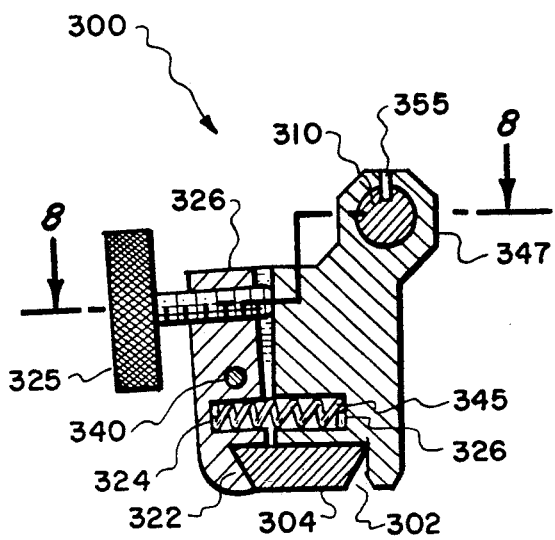
FIG. 7 is a cross-sectional view taken along the lines 7—7 of FIG. 2 showing the cross-sectional view of the V-clamp, also known as the side arm clamp.

The various clamps in conjunction with the present invention will now be discussed in further detail. The first major clamp referred to as the V-clamp, or side arm clamp 300, is shown in detail in FIGS. 7 through 9. The V-clamp has a channel-shaped mounting surface 302 such that it can slide back and forth on either the stationary arm 40 or the moveable arm 25. The railing portion 304 of either arm can have a wedge shape in cross section as illustrated in FIG. 7. The V-clamp can be mounted on either arm, and it can be mounted facing the chest cavity, or mounted facing away from the chest cavity. The purpose of this V-clamp is to hold a cylindrical support rod 310 parallel to the arm that the V-clamp is attached to. The V-clamp is moveable by the surgeon along the railing portion 304 of the arm. There is a grooved rocker 320 mounted vertically to the frame 348 of the clamp, and the lower grooved portion 322 of the rocker 320 functions to press against the edge of the rail 304 to lock the side arm clamp into position. The locking is accomplished by a knurled screw 325 threadably secured to the upper end 326 opposite the grooved end of the rocker. The rocker in turn is secured to the main frame 348 of the V-clamp by positioning it into a rectangular vertical grooved recess 330 having a transversely drilled hole 335 which goes through the frame and through the grooved rocker. Into this hole is a pivot retaining pin or screw 340. There is a spring 345 positioned between the frame and the lower portion of the rocker to spring bias the grooved rocker outwardly when the knurled screw 325 is not tightened down. Hole 324 in the grooved rocker and hole 326 in the recess hold the spring in place. Spring 345 keeps the rocker at the bottom of the V-clamp open to allow easy movement of the V-clamp along the rail portion of either arm. After the clamp is slid to the desired position, then the surgeon simply turns the knurled screw 325 which in turn causes the grooved rocker 320 to pivot about the pivot retaining screw 340 forcing the grooved bottom 322 of the rocker against the edge of the railing of the arm to frictionally hold the arm in the channel 302 formed at the base of the frame of the V-clamp. There is a longitudinal bore 345 drilled in a shoulder 347 extending from the upper portion of the frame 348 of the V clamp 300. The bore 345 further has a pair of notches 350 cut away adjacent either end of the bore. The bore is used to receive one end of the support rod 310. The support rod further has an alignment pin 355 transversely secured into the surface wall of the cylindrical support rod. The alignment pin mates with either notch 350 adjacent the bore 345 in the shoulder portion of the frame 348 to prevent the support rod 310 from rotating about its axis. The support rod has at one end has a tapered threaded end 360 which extends through the bore 345. The alignment pin also limits how far the threaded end can extend beyond the other end of the bore. This threaded end is held in place by knurled nut 365 which is screwed on to the threaded end. It maintains the support rod 310 in position and prevents it from rotating about it axis. The support rod is used to hold the castellated clamp 400 and articulated extension rod, or to hold the universal clamp 500 along the support rod 310. This is shown in FIG. 1 where the castellated clamp 400 is clamped on to the support rod 310, and there is also illustrated a universal clamp 500 also attached to the support rod.

The second clamp, referred to as the castellated clamp 400, is illustrated in detail in FIGS. 10–13. The castellated clamp has an integral extension rod 410 that is permanently secured at a right angle to the bolt portion 420 of the clamp. The bolt portion 420 has a cylindrically shaped head 425, a shoulder 421, and a smaller threaded shaft 430 extending concentrically from the bottom of the head 425. The inner circular face of the circular head has radial V-grooves forming a castellated surface 435.

The other portion of this castellated clamp is generally described as a U-shaped clamp 440 which forms a bore 445 at its bight for clamping onto the support rod 310. There is a side slit 442 in the bight area of the clamp, and a longitudinal groove 443 in the wall of bore 445. The U-shaped clamp can be compressed or squeezed together to secure the clamp in place on the support rod, or any other rod. The U-shaped clamp has a clearance between top and the bottom, so that the ends 450 can be squeezed, or compressed together so that the bore formed in the bight area of the U-shaped clamp can form a compression fit around the support rod 310. The ends of the U-shaped clamp have a common bore 455 drilled there through for receiving the threaded end 430 and the shoulder 421 of the castellated bolt 420. Bore 455 is orthogonal to the bight bore 445. The concentric surface around one end of the bore 455 likewise has a castellated surface 460, or radially cut V-shaped grooves that will mate with the castellated cuts on the inner surface 435 of the bolt head so that the complementary fitting of these castellated surfaces will prevent rotation or other articulated movement of the extension rod 410 once everything is tightened down. Clamp 440, and the extension rod 410 and bolt head 425 combination are tightened down together by a knurled nut 462 screwed onto the threaded end 430 of the bolt extending through the drilled bore 455 at the end of the U-shaped clamp. The shoulder 421 is the same diameter as bore 455 to prevent movement of the bolt 420 in the bore 455. Turning and tightening down the knurled nut serves two functions; one is to pinch the U-shaped clamp 440 together to frictionally hold itself in a stationary position on the support rod 310, and secondly to force the castellated surfaces 435 & 460 together to prevent the extension rod 410 from changing positions after it has been locked into place. The resistance to the ends 450 being compressed together also assists in keeping the nut 462 from turning and loosening. This clamp allows the surgeon versatility in moving the articulated extension arm 410 back and forth along one of the major arms 25 & 40, and secondly, the extension rod 410 can be angularly adjusted and positioned independently of the support rod 310 by angularly changing the relationship between the castellated bolt 420 and the castellated U-shaped clamp 440.

Figure 14:
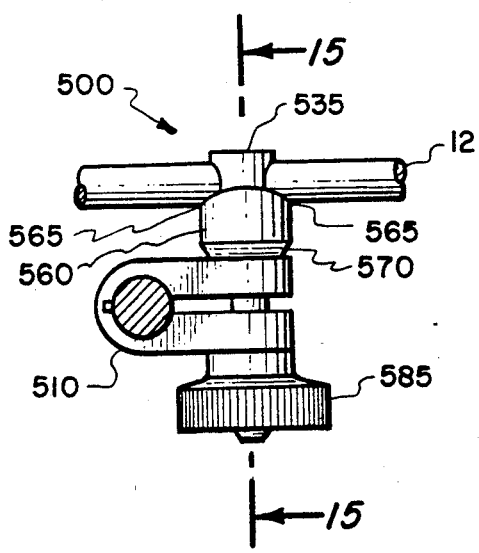
FIG. 14 is a view taken along the lines 14—14 of FIG. 1 showing a front elevational view of the universal mount clamp shown in FIG. 1.
Figure 15:
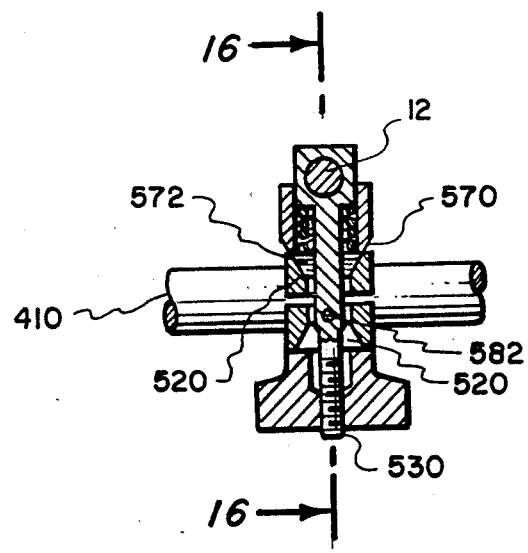
FIG. 15 is a cross-sectional view taken along the lines 15—15 of FIG. 14 showing the cross-sectional view of the universal mount clamp.
Figure 16:
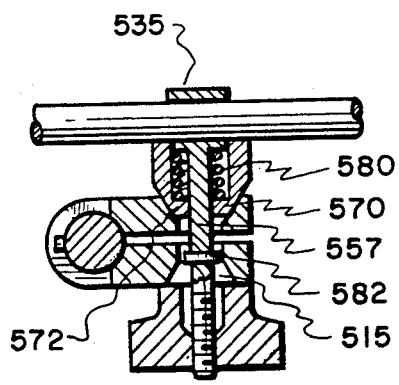
FIG. 16 is a second cross-sectional view taken along the lines 16—16 of FIG. 15 further showing another cross-sectional of the universal clamp.
Figure 17:
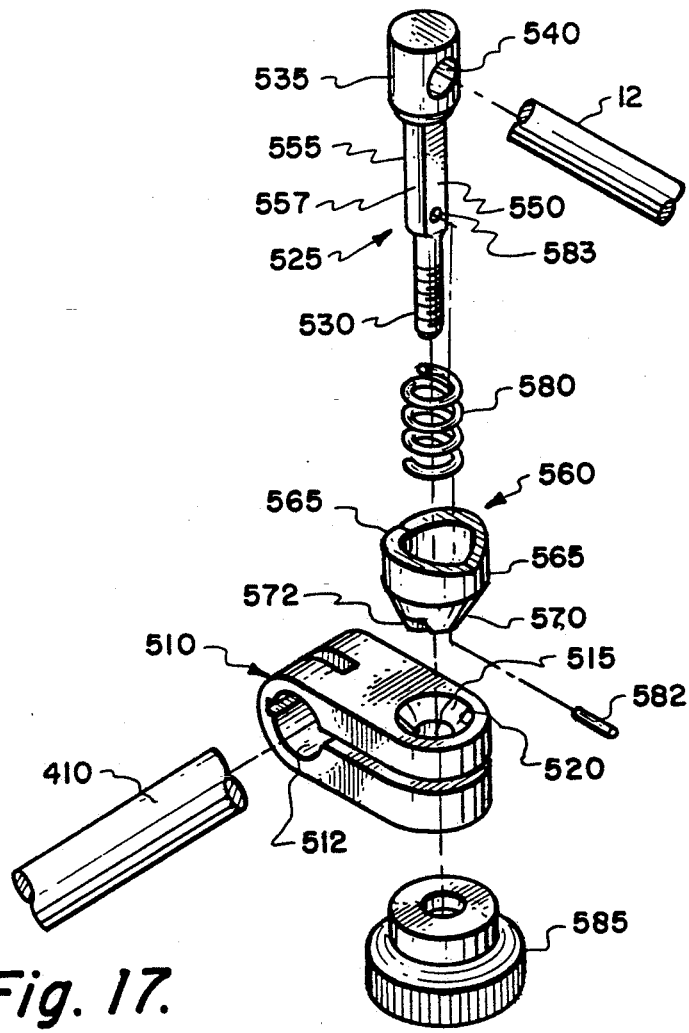
FIG. 17 is an exploded perspective view showing the uniclamp and its various components and how they cooperate one another.

The third clamp is referred to as the universal clamp 500. It is illustrated in detail in FIGS. 14-17. This clamp usually is used in conjunction with the end of the extension rod 410 extending from the castellated clamp 400. However, the universal clamp also can be used as an intermediary clamp between the support rod 310 and the shank 12 of one of the retractors 10 or 15. In the arrangement shown in FIG. 1, the universal clamp is secured to the far end of the castellated extension rod 410. The clamp in turn holds the shank of the aortic valve retractor 10 or mitral valve retractor blade 15. The universal clamp also has a U-shaped clamp 510 almost identical to the clamp 440 used in the castellated clamp 400. However, instead of having a castellated surface around the circumference of the opening of the drilled bore 515 for holding the bolt, the concentric area 520 surrounding the entrance to the bore is countersunk, rather than castellated. The opposite opening of the bore 515 is also countersunk. The bolt 525 has a threaded end 530, a neck 557, and a cylindrically shaped head 535. There is a diametral transverse bore 540 drilled in the bolt head for holding the shank of the retractor blade 12 as illustrated in FIG. 14. The rounded neck of the bolt further has a pair of opposed longitudinal flat planar surfaces 550 & 555 formed by removing secant flat sections from opposite sides of the neck of the bolt. Each of these two planar surfaces is perpendicular to and at a right angle to the axis of the diametral bore 540. The cross-section of the neck 557 has a flattened oval shape. The flattened planar surfaces 550 & 555 of the neck slideably engage with a hollow, inverted cone tipped cylinder 560 that has a pair of diametral transverse V-shaped grooves 565 cut away at the base of the cylinder opposite the tip 570. The tip 570 of the cone tipped cylinder is pointed downwardly towards the threaded end 530 of the bolt 525. The V-shaped grooves 565 face toward the bolt head 535. The coned cylinder 560 has a transverse slotted opening 572 cut away at its tip 570. The slotted opening 572 is similar in shape to the flattened oval cross section of the neck 557 of the bolt so that the slotted opening 572 will engage with and slide on the pair of opposed flattened surfaces 550 & 555 of the neck 557 of the bolt 525. The imaginary longitudinal median line of the slotted opening 572 at the tip of the cone is at a right angle relative to the imaginary line extending between the apexes made by the V-shaped grooves 565 at opposite sides of the top rim of the cone tipped cylinder. The transverse slotted opening 572 prevents the cone tipped cylinder from rotating independently of the bolt itself, to which it is slideably engaged. Additionally, there is a coil spring 580 positioned around the neck 557 of the bolt 525 and having one end inside and abutting the hollowed out cylinder 560, and the other end abutting the base of the round head 535 to spring bias the cone tipped cylinder 560 along the neck 557 of the bolt 525. There is also a cotter pin 582 positioned in a hole 583 at the base of the flattened neck portion of the bolt and just before the threaded end. This prevents the cone tipped cylinder 560 from disengaging from the bolt 525. The spring 580 presses against the cylinder 560, and the cylinder would slide off the threaded end 530 of the bolt 525 if the cotter pin 582 were not present to stop it. The length of the cylinder 560 is less than the length of the neck portion 557.

The brite of the U-shaped clamp 510 has a bore 512 there through for slideably engaging with and frictionally clamping onto either the extension rod 410 of the castellated clamp 400, or with the support rod 310 positioned parallel to the support arms 25 & 40. Both are the same diameter. There is a knurled nut 585, which screws on to the threaded end 530 of the bolt. It can be tightened down to clamp the U-shaped clamp 510 around one of the rods. The diameter of the cylindrical nut head 535 is slightly smaller than the diameter of the hollowed out opening in the base of the cone tipped cylinder 560.

During the tightening down process, after the shank 12 of the retractor has been inserted into the bore 540 of the bolt head, the bolt head 535 with the transversely held shank 12 will be pulled into the opening of the upwardly projecting hollowed out base of the cylinder and the V-shaped cutaways 565 in the circular rim of the cylinder. The opposed slanted edges of the rim form a cradle-like structure to frictionally contact the shank and lock the shank of the retractor so that it cannot slide or turn in the bore 540 of the bolt head as it is transversely cradled, or held in place. The upper wall of the bore 540 also frictionally presses against the shank of the retractor also to prevent it from moving. The cone tip 570 of the cylinder 560 also enters and docks with the wall 250 of the counter sunk hole 515, which also assists in preventing the bolt 525 and attached retractor from turning. By turning the knurled nut 585, it locks into position the angular orientation chosen by the surgeon. The retractor will not change position, because it is securely locked into place. The shank of the retractor is forced down into the V-shaped depressions 565 of the cylinder by means of the knurled knob being turned clockwise and pulling the circular head 535 with the shank into the V-shaped depressions thereby preventing the attached mitral or aortic valve from rotating or slipping while in position. The imaginary line of the axis of the bore 540 in the bolt head 535 will always align with the imaginary line drawn between the apexes of the opposed V-shaped grooves 565 cutaway in the rim of the cylinder.

The clamp 510 forms a mirror image of itself along the gap between both ends of the clamp. This is useful when the clamp is dissembled, washed and sterilized after use, and reassembled for the next operation. The bolt 525, spring 580, and cylinder 560 subassembly stay together because of the coter pin 582. This subassembly can be inserted in either opening of the bore 515. The knurled nut 585 can screw on to the bolt from either side of the nut. All of These features are intended to prevent the clamp from being reassembled incorrectly after cleaning.

DISCUSSION OF THE BOOT CLIP

The boot clip 600, which is about 5 inches long, is illustrated in detail in FIGS. 25-26. Three boot clips also are shown in FIG. 1. One is clipped onto the stationary arm 25, another to the tooth cross bar 30, and yet another to the moveable arm 40. The boot clip can be fabricated from an elongate flat piece of metal. A perpendicular edge, or lip 610, is formed by bending along a line parallel to and inboard from one of the long sides thus forming an L-shaped channel bar 600, in cross section. The flat face 630 has two holes 640 & 650 drilled towards either end. A coiled spring 660 having hooked ends 680 & 690 and having an overall length slightly less than the distance between the two holes is stretched out so that the hooked ends can be secured to the holes. The spring is slightly tensioned by both hooked ends pulling on the spring. Medially attached to the lip 610 of the bar 600 is a resilient clip 665 that extends below and parallel to the flat face 630. The resilient clip is secured by rivets 670.

The boot clip is clipped onto one of the arms by sliding the arm between the resilient clip and face as shown in FIG. 25. The resilient clip anchors and keeps the boot clip from sliding too easily back and forth on the arm, and the lip 610 will prevent the clip from moving transversely on the arm when the boot clip is used during certain procedures during open heart surgery. The structure of the boot clip can be modified. It could be a channel shape in cross section with both sides sufficiently resilient to spread apart and grip the arm and hold the boot clip in place. The tensioned spring is the important part of the boot clip. The function of the boot clip and its use by the surgeon is described in the Summary and Operation of the Invention, supra.

While the present invention has been shown and described herein in what is conceived to be the best mode contemplated, it is recognized that departures may be made therefrom within the scope of the invention which is therefore not to be limited to the details disclosed herein, but is to be afforded the full scope of the invention.

What is claimed is:

1. A valve retractor and sternum spreader surgical instrument comprising:
   a stationary arm having a first end and a second end;
   a toothed cross bar also having a first end and a second end, said toothed cross bar first end being secured to said first end of said stationary arm in a generally perpendicular relation and forming a generally L-shaped section;
   a moveable arm having a first end and a second end;
   said first end of said movable arm having a housing with a slotted opening which is attachable to said toothed cross bar and is laterally moveable along the length of said cross bar;
   a pair of load bearing swivel inserts demountably secured in said housing for containing and guiding said cross bar within said slotted opening of said housing on said moveable arm;
   said pair of load bearing swivel inserts comprises:
   a first insert and a second insert positioned separately in two swivel insert holes in said housing, said swivel insert holes being staggered and on opposite sides relative to said cross bar;
   said inserts are removable and can swivel in said swivel insert holes to allow said housing and said moveable arm to pivot slightly relative to said toothed cross bar to prevent said toothed cross bar from binding in said housing while said device is in use;
   each of said first and second inserts being cylindrical in shape;
   at least said first insert having a first secant flat width cut away laterally for creating a sliding surface, said width of said first secant flat being slightly larger than the thickness of said toothed cross bar so that said toothed cross bar can freely slide back and forth in said first secant flat cutaway;
   said first scant flat having a chord face, an upper secant portion, and a lower secant portion;
   rack and pinion means in said housing for moving said moveable arm along the length of said cross bar;
   said stationary arm and said moveable arm being in a spaced parallel relationship with each other and able to open and close parallel to each other by rotating said rack and pinion means in said housing of said moveable arm;
   both said moveable arm and said stationary arm having a plurality of swivel blades connected to them and extending below such that said blades can engage the walls of a surgically cut opening on a patient and said movable arm can be extended away from said stationary arm by rotating said rack and pinion means to spread apart and hold open the walls of the opening thereby exposing a body cavity for allowing the surgeon to operate.

2. The device as recited in claim 1 wherein said second insert is also cylindrically shaped and has a second secant flat width cut away laterally for creating a sliding surface, said width of said second secant flat being slightly larger than the thickness of said toothed cross bar so that said toothed cross bar can freely slide back and forth in said second secant flat;
   said second insert comprising a lower body being cylindrical in shape and having a flat top with a secant portion removed from it forming an upper secant portion of said flat top, a vertical ledge, and a lower secant flat portion;
   a cylindrical cap having the same diameter as said cylindrical lower body, said circular cap being demountably secured to said upper secant portion of said flat top with a screw;
   retaining pin means interconnecting said circular cap with said lower body to prevent said cap from turning relative to said lower body of said insert;
   said cap, said ledge, and said lower second secant portion forming said secant flat.

3. The device as recited in claim 1 wherein said face of said first secant flat has a metal overlay of either tungsten carbide or 55 series bronze.

4. A valve retractor and sternum spreader surgical instrument comprising:
   a stationary arm having a first end and a second end;
   a toothed cross bar also having a first end and a second end, said toothed cross bar first end being secured to said first end of said stationary arm in a generally perpendicular relation and forming a generally L-shaped section;

a moveable arm having a first end and a second end;

said first end of said movable arm having a housing with a slotted opening which is attachable to said toothed cross bar and is laterally moveable along the length of said cross bar;

a pair of load bearing swivel inserts demountably secured in said housing for containing and guiding said cross bar within said slotted opening of said housing on said moveable arm;

said pair of load bearing swivel inserts comprises:

a first insert and a second insert positioned separately in two swivel insert holes in said housing, said swivel insert holes being staggered and on opposite sides relative to said cross bar;

said inserts are removable and can swivel in said swivel insert holes to allow said housing and said moveable arm to pivot slightly relative to said toothed cross bar to prevent said toothed cross bar from binding in said housing while said device is in use;

each of said first and second inserts being cylindrical in shape;

rack and pinion means in said housing for moving said moveable arm along the length of said cross bar;

said stationary arm and said moveable arm being in a spaced parallel relationship with each other and able to open and close parallel to each other by rotating said rack and pinion means in said housing of said moveable arm;

both said moveable arm and said stationary arm having a plurality of swivel blades connected to them and extending below such that said blades can engage the walls of a surgically cut opening on a patient and said movable arm can be extended away from said stationary arm by rotating said rack and pinion means to spread apart and hold open the walls of the opening thereby exposing a body cavity for allowing the surgeon to operate.

5. A valve retractor and sternum spreader surgical instrument comprising:

a stationary arm having a first end and a second end;

a toothed cross bar also having a first end and a second end, said toothed cross bar first end being secured to said first end of said stationary arm in a generally perpendicular relation and forming a generally L-shaped section;

a moveable arm having a first end and a second end;

said first end of said movable arm having a housing with a slotted opening which is attachable to said toothed cross bar and is laterally moveable along the length of said cross bar;

a pair of load bearing swivel inserts demountably secured in said housing for containing and guiding said cross bar within said slotted opening of said housing on said moveable arm;

said pair of load bearing swivel inserts comprises:

a first insert and a second insert positioned separately in two swivel insert holes in said housing, said swivel insert holes being staggered and on opposite sides relative to said cross bar;

said inserts are removable and can swivel in said swivel insert holes to allow said housing and said moveable arm to pivot slightly relative to said toothed cross bar to prevent said toothed cross bar from binding in said housing while said device is in use;

each of said first and second inserts being rectangular shaped or semicircular shaped with a hole for receiving a pivot pin therethrough;

first and second pivot pins for holding each said first and second inserts in position;

said two swivel insert holes having the same diameter as each said pivot pin for holding said pivot pin and said insert in said arm;

rack and pinion means in said housing for moving said moveable arm along the length of said cross bar;

said stationary arm and said moveable arm being in a spaced parallel relationship with each other and able to open and close parallel to each other by rotating said rack and pinion means in said housing of said moveable arm;

both said moveable arm and said stationary arm having a plurality of swivel blades connected to them and extending below such that said blades can engage the walls of a surgically cut opening on a patient and said movable arm can be extended away from said stationary arm by rotating said rack and pinion means to spread apart and hold open the walls of the opening thereby exposing a body cavity for allowing the surgeon to operate.

* * * * *